(12) United States Patent
Barkow et al.

(10) Patent No.: US 7,744,278 B2
(45) Date of Patent: Jun. 29, 2010

(54) X-RAY DEVICE WITH A SCATTERED RAY PROTECTION DEVICE

(75) Inventors: Kerstin Barkow, Bad Neustadt a. d. Saale (DE); Franz Beimler, Weiden (DE)

(73) Assignee: Siemens Aktiengesellschaft, Munich (DE)

( * ) Notice: Subject to any disclaimer, the term of this patent is extended or adjusted under 35 U.S.C. 154(b) by 181 days.

(21) Appl. No.: 11/659,638

(22) PCT Filed: Aug. 4, 2005

(86) PCT No.: PCT/EP2005/053849
§ 371 (c)(1),
(2), (4) Date: Feb. 5, 2007

(87) PCT Pub. No.: WO2006/018395
PCT Pub. Date: Feb. 23, 2006

(65) Prior Publication Data
US 2008/0031422 A1 Feb. 7, 2008

(30) Foreign Application Priority Data
Aug. 13, 2004 (DE) ................. 10 2004 039 411

(51) Int. Cl.
*H01J 35/16* (2006.01)
(52) U.S. Cl. .................................................. 378/203
(58) Field of Classification Search .............. 378/203, 378/62; 250/515.1; *G21F 3/00*
See application file for complete search history.

(56) References Cited

U.S. PATENT DOCUMENTS 4,214,167 A * 7/1980 Gade ....................... 378/147
5,704,728 A * 1/1998 Chan ........................ 403/298
5,940,470 A * 8/1999 Palm-Plessmann et al. . 378/197
6,325,538 B1 * 12/2001 Heesch ..................... 378/203
2003/0091156 A1 5/2003 Crain et al.

(Continued)

FOREIGN PATENT DOCUMENTS

DE 30 46 532 A1 7/1982

(Continued)

OTHER PUBLICATIONS

Machine translation of DE3046532, 1982.*

(Continued)

*Primary Examiner*—Edward J Glick
*Assistant Examiner*—Mona M Sanei
(74) *Attorney, Agent, or Firm*—Brinks, Hofer, Gilson & Lione (57) ABSTRACT

An x-ray device is provided. The x-ray device includes an x-ray emitter, an image receiver arranged in a radiation direction at a distance from the x-ray emitter, a patient support disposed between the x-ray emitter and the image receiver, a relative position of the x-ray emitter and the image receiver being adjustable with respect to the patient support in at least one spatial direction, and a scattered ray protection device, which can be fixed in a fixed relative position with respect to the image receiver and/or the x-ray emitter as a reference object using a coupling unit the scattered ray protection device being entrained with the reference object when the reference object is adjusted with respect to the patient support.

14 Claims, 7 Drawing Sheets

U.S. PATENT DOCUMENTS

| | | |
|---|---|---|
| 2004/0091082 A1 | 5/2004 | Brendel et al. |
| 2005/0058257 A1 | 3/2005 | Fischer et al. |

FOREIGN PATENT DOCUMENTS

| | | |
|---|---|---|
| DE | 30 46 532 C2 | 7/1982 |
| DE | 297 06 321 U1 | 7/1997 |
| DE | 203 07 606 U1 | 9/2003 |
| DE | 203 07 606 U1 | 10/2003 |
| DE | 103 32 743 A1 | 3/2005 |
| EP | 0 393 214 A1 | 4/1989 |
| EP | 0 393 214 A | 10/1990 |
| WO | WO 02/00116 A1 | 1/2002 |

OTHER PUBLICATIONS

German Office Action dated Oct. 25, 2005 for DE 10 2004 039 411.1-35 and translation.

German Office Action dated Mar. 31, 2006 for DE 10 2004 039 411.1-35 and translation.

* cited by examiner

X-RAY DEVICE WITH A SCATTERED RAY PROTECTION DEVICE

The present patent document is a §371 continuation of PCT Application Serial Number PCT/EP2005/053849, filed Aug. 4, 2005, designating the United States, which is hereby incorporated by reference. This patent document also claims the benefit of DE 10 2004 039 411.3, filed Aug. 13, 2004.

The present embodiments relate to a medical x-ray device having an x-ray emitter, an image receiver arranged in a radiation direction at a distance from said x-ray emitter and a patient support arranged between the x-ray emitter and the image receiver. The relative position of the x-ray emitter and the image receiver is adjustable with respect to the patient support in at least one spatial direction vertically or transversally to the radiation direction. An x-ray device of this type is described in WO 02/00116 A1.

With certain medical x-ray examinations, in particular with fluoroscopy methods using contrast agents as well as with x-ray-assisted operations and interventions, the treating medic must maintain his/her position directly adjacent to the radiated patient during the irradiation process, and is exposed to comparatively intensive scattered radiation from the body of the patient.

In order to minimize the radiation exposure for the treating medic under these conditions, the treating medic wears radiation protective clothing, in particular lead aprons, thyroid protection, and other suitable clothing. Moveable radiation protective screens made of lead acrylic glass may also be used. A moveable radiation protective screen is mostly attached to a single-jointed or multiple-jointed arm on the ceiling or a wall of the examination room and may be positioned freely in the room to a limited degree. Generally, a radiation protection device of this type is comparatively bulky in terms of size and weight and hinders the examination activity of the treating medic. A radiation protection screen is a hindrance in that it must frequently be moved manually when the position of the x-ray beam, the image receiver, or the patient is changed with respect to the treating medic, in order to continue to protect the medic against the changed scattered radiation field. A conventional radiation protection screen may get in the way of an adjustment of the x-ray device.

SUMMARY

The present embodiments may obviate one or more of the limitations or drawbacks inherent in the related art. For example, in one embodiment, an x-ray device has an effective scattered ray protection device. The device for the treating medic is particularly easy to handle, with the intention being, in particular, to prevent the examination activity of the medic from being hindered as far as possible by the scattered ray protection device.

In one embodiment, an x-ray device includes an x-ray emitter, an image receiver arranged in a radiation direction at a distance from said x-ray emitter, and a patient support arranged between the x-ray emitter and the x-ray receiver. The x-ray receiver is a functional unit that positions and centers a film cassette. A support unit for an x-ray image amplifier or a digital x-ray detector can also be used as an image receiver. The patient support is a patient bed.

In one embodiment, the x-ray emitter and the x-ray receiver can be adjusted mutually and/or individually in relation to the patient support and in at least one spatial direction, vertically or transversally, to the radiation direction. Preferably both can be adjusted in the longitudinal direction and also in the transverse direction, with regard to the patient support. Alternatively or in addition, the patient support is adjustable so that the respective relative position of the x-ray emitter and of the image receiver can be changed in relation to the patient support.

In one embodiment, a scattered ray protection device is provided. The scattered ray protection can be fixed in at least one fixed relative position in an adjustment direction of the reference object with respect to the image receiver and/or the x-ray emitter. The fixing is designed such that with an adjustment of the reference object (i.e. depending thus on the design of the image receiver and the x-ray emitter), with respect to the patient support, the scattered ray protection device is also correspondingly adjusted in relation to the patient support.

The intensity of the scattered radiation at a spatial point in the vicinity of an x-ray device essentially depends on the relative position of the observed spatial point at the treatment location where the central beam of the x-ray radiation penetrates a patient undergoing treatment. The treatment location depends on the local arrangement of the x-ray emitter and the image receiver. The scattered radiation field 'migrates' with an adjustment of the image receiver and/or x-ray emitter compared with the patient support. By coupling the scattered ray protection device to the image receiver and/or the x-ray emitter as a reference object, protection remains the same for the treating medic at any point in time during an examination and also during the adjustment of the reference object.

In one embodiment, the scattered ray protection device is positioned with respect to the reference object such that it is arranged in the main field of the imminent scattered radiation. A suitable relative position of the scattered ray protection device can be defined by determining the central beam of the primary beam field emitted by the x-ray emitter in the direction of the image receiver.

By entraining the scattered ray protection device with the reference object, the operation can be considerably simplified for the treating medic because the need for a manual adaptation of the scattered ray protection device during the examination is avoided. By entraining the scattered ray protection device with the reference object, any collision of the scattered ray protection device with any components of the x-ray device is eliminated when the latter is adjusted.

In one embodiment, the scattered ray protection device is designed as a self-supporting, essentially rigid screen. The same scattered ray protection device may be used in different orientations of the x-ray devices, in particular with a horizontally or vertically aligned patient support. In contrast to this, a scattered ray protection device composed of lead plates, for example, as is conventionally and frequently used, would collapse back upon itself if the table is repositioned.

In one embodiment, the scattered ray protection device includes a flat body panel to protect the upper body of the treating medic. The plane of this body panel is aligned approximately parallel to a front edge of the patient support, so that the body panel is disposed horizontally to a support surface of the patient support or is inclined slightly thereover. A viewing panel is fitted on an upper edge of this body panel. The viewing panel is angled away from the body panel in the direction towards the patient support. The viewing panel is preferably configured to be integral with the body panel, in particular in one-piece. The viewing panel allows the treating medic to bend over the body panel to the patient support during the examination, without being exposed to an increased radiation exposure in the head region. The viewing panel allows the medic to adopt a similar examination position, as he would conventionally adopt in the absence of the scattered ray protection device, and thus boosts the manageability of the x-ray device. The edge of the body panel is referred to as the upper edge of the body panel (irrespective of the actual orientation of the body panel in the surrounding room). The body panel faces away from the support surface of the patient support bed.

At least one side edge with a concave recess or cut-out is provided by the side edges of the body panel bordering the upper edge. The body panel includes a laterally waisted shape. The waist of the body panel, which is formed by the recess or any recess, allows the medic's arms to be moved around the radiation protection device during a medical treatment while at the same time providing an effective radiation protection for the lower body, the head, and the shoulder region of the treating medic.

In one embodiment, a moveable sliding panel is arranged on at least one edge of the body panel, in particular on one or both side edges. At least one sliding panel is positioned such that it enlarges the surface shielded by the body panel in a normal position in order to optimize the radiation protection and can be moved from this normal position into a release position, which is withdrawn at least partially into the surface region of the body panel, in order to assist in allowing arm movements around the body panel. The sliding panel is arranged so that in the normal position it at least partially covers a recess provided in a side edge of the body panel.

In one embodiment, the unit is simple to handle for the treating medic and ensures a particularly good protective function. The at least one sliding panel is able to be moved against a restoring force elastically from its normal position and to automatically revert to its normal position from the moved state, particularly on release. Such an automated restoration of the at least one sliding panel is realized by mounting at least one sliding panel eccentrically in a pivotable fashion, for example, at a distance from its center of gravity, so that the force of gravity acting on the sliding panel operates as a restoring force and the sliding panel presses back into the normal position during a movement.

Alternatively or in addition, a spring element is assigned to the at least one sliding panel. The spring element generates or optionally amplifies the restoring force. The optionally provided spring element ensures that the at least one sliding panel is always restored to its normal position, even with a rotation of the radiation protection device, particularly if the patient support is moved from a horizontal position into a vertical position. Alternatively, a fixing element is assigned to the at least one sliding panel, in particular in the form of a fixing screw, a magnetic catch or a snap-on seal, or any suitable device which the at least one sliding panel can be fixed at least in the normal position, or optionally in further fully or partly withdrawn positions.

In one embodiment, during a pause in the irradiation process, the scattered ray protection device is removed from the relative position with respect to the relative object (i.e. of the image receiver and/or x-ray emitter). This particularly facilitates the execution of medical treatment steps and other treatments, which are to be carried out prior to or after the actual radiation phase, in particular the positioning of a patient on the patient support, but also the cleaning of the x-ray device.

In one embodiment, to remove the scattered ray protection device from the relative position, the coupling unit allows the scattered ray protection device to be pivoted out of and/or into the relative position. The coupling unit is configured such that the scattered ray protection device is completely detached from the reference object. A detachable connection of the scattered ray protection device is realized constructively in a particularly simple manner by a coupling unit designed as a plug-in connector.

In one further embodiment, the control and monitoring elements for the x-ray device are arranged on the front side of the scattered ray protection device facing the treating medic.

To ensure the treating medic has a good view of the patient to be treated, the scattered ray protection device is at least essentially formed from a transparent x-ray-absorbent material. Lead acrylic glass is suitable for use in manufacturing the scattered ray protection device.

DETAILED DESCRIPTION

Figure 1:
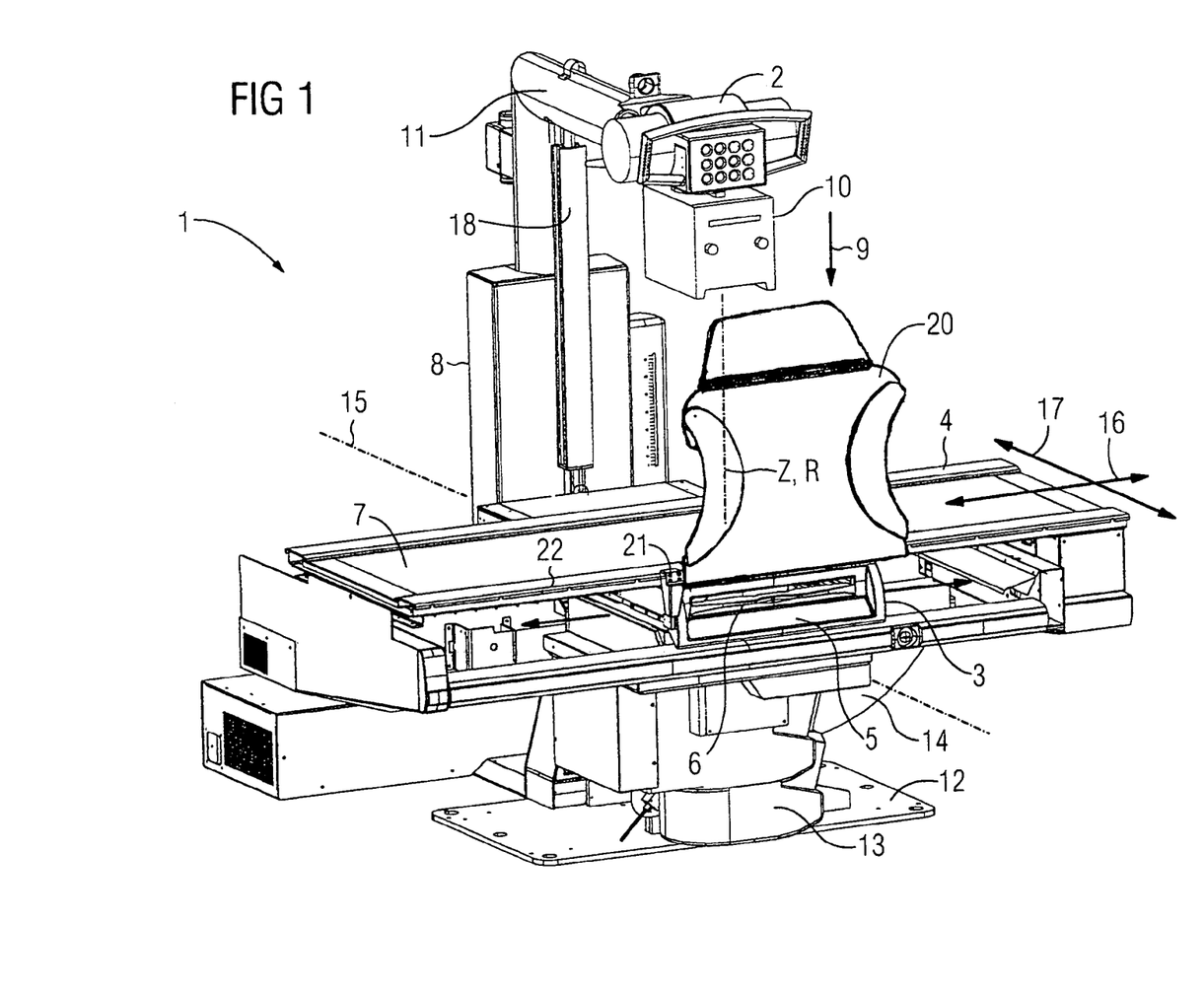
FIG. 1 is a perspective view of the front side of one embodiment of an x-ray device.

In one embodiment, as shown in FIG. 1, the x-ray device 1 includes an x-ray emitter 2, an image receiver 3 and a patient support 4. The image receiver 3 is a functional unit, into which a film cassette having an x-ray film can be positioned. To allow the film cassette to be inserted, the image receiver 3 is provided on a front side 5 with a corresponding insertion slit 6 for the film cassette. The patient support 4 is a patient bed. As shown in FIG. 1, the support surface 7 is horizontally aligned.

The x-ray emitter 2, the image receiver 3 and the patient support 4 are mounted on a common stand 8. The image receiver 3 is disposed at a distance opposite to the x-ray emitter 2, viewed in a radiation direction 9. The support surface 7 of the patient support 4 is arranged between the image receiver 3 and the x-ray emitter 2.

In one embodiment, as shown in FIG. 1, the support surface 7 is essentially aligned horizontally to the radiation direction 9. The x-ray emitter 2, together with a diaphragm 10 arranged upstream in the radiation direction 9, is affixed to a gallows-like emitter support 11 of the stand 8.

Figure 2:
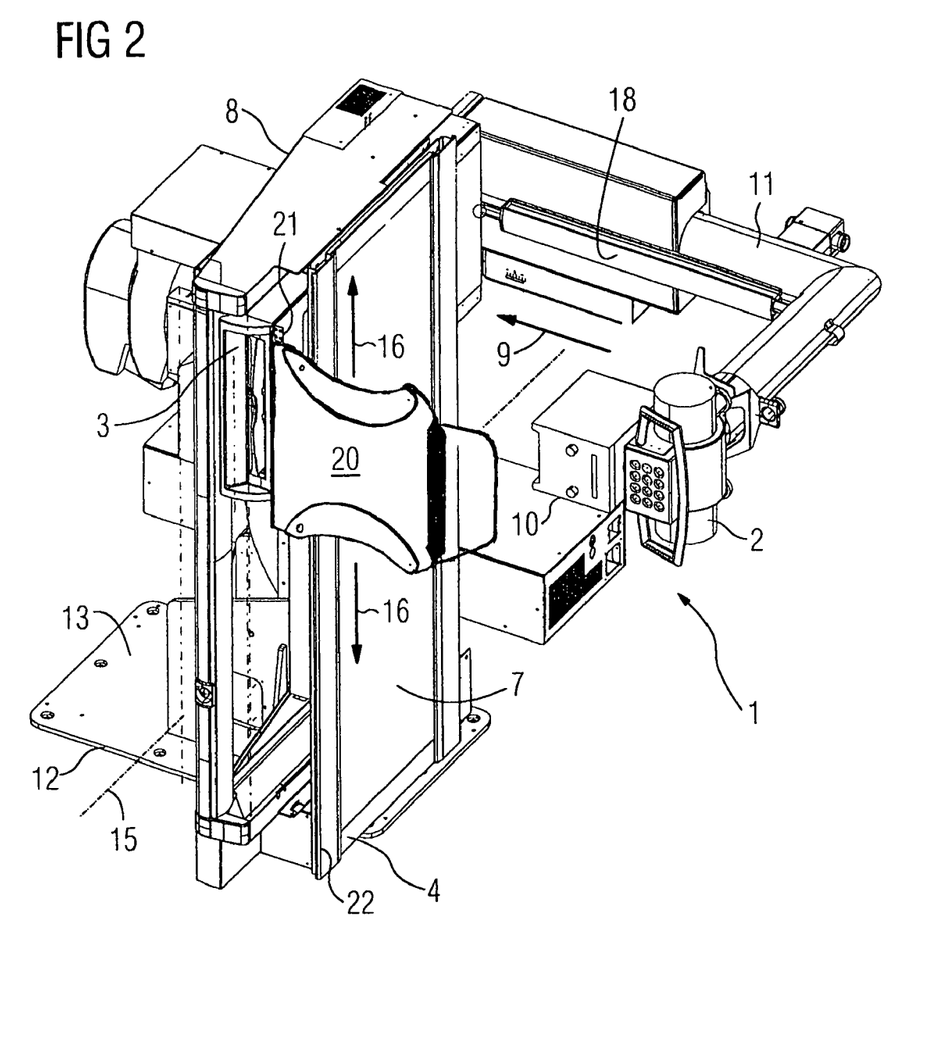
FIG. 2 is a perspective view of one embodiment of the x-ray device in a stand position rotated by 90°, according to a horizontal arrangement of the patient support.

The stand 8 includes a stand base 13 fixed by a base plate 12 and a dolly 14. The dolly 14 is mounted in a pivotable manner on the stand base 13 about a rotary axis 15 running horizontally and transversally with respect to the support surface 7 of the patient support 4. The dolly 14 supports the patient support 4. The support surface 7 can be adjusted by pivoting the dolly 14, in particular from the horizontal position shown in FIG. 1 into a vertical position according to FIG. 2. The dolly 14 supports the image receiver 3 and the emitter support 11 with the x-ray emitter 2, which rotate with the described pivoting of the dolly 14 with the patient support 4. The radiation direction 9, which is vertical compared with the surrounding room according to FIG. 1, is also pivoted in a horizontal orientation (FIG. 2).

Figure 6:
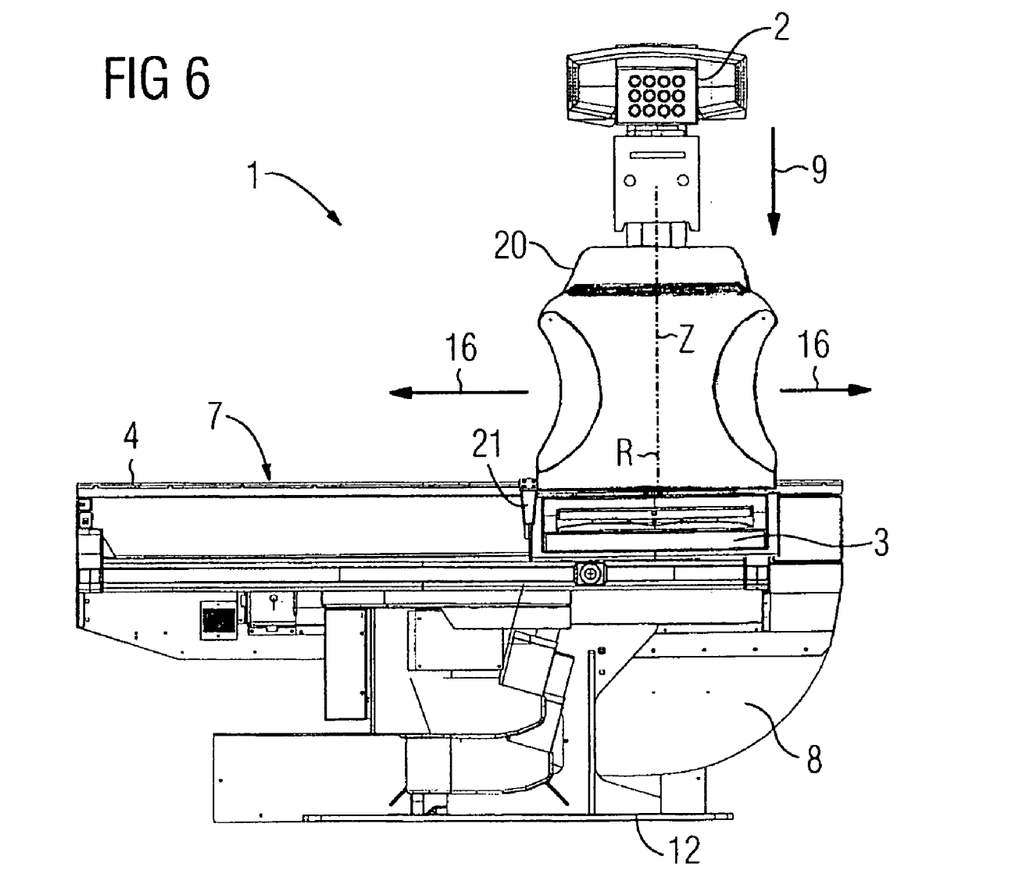
FIG. 6 is a front view of one embodiment of the x-ray device with an image receiver and an entrained scattered ray protection device.
Figure 7:
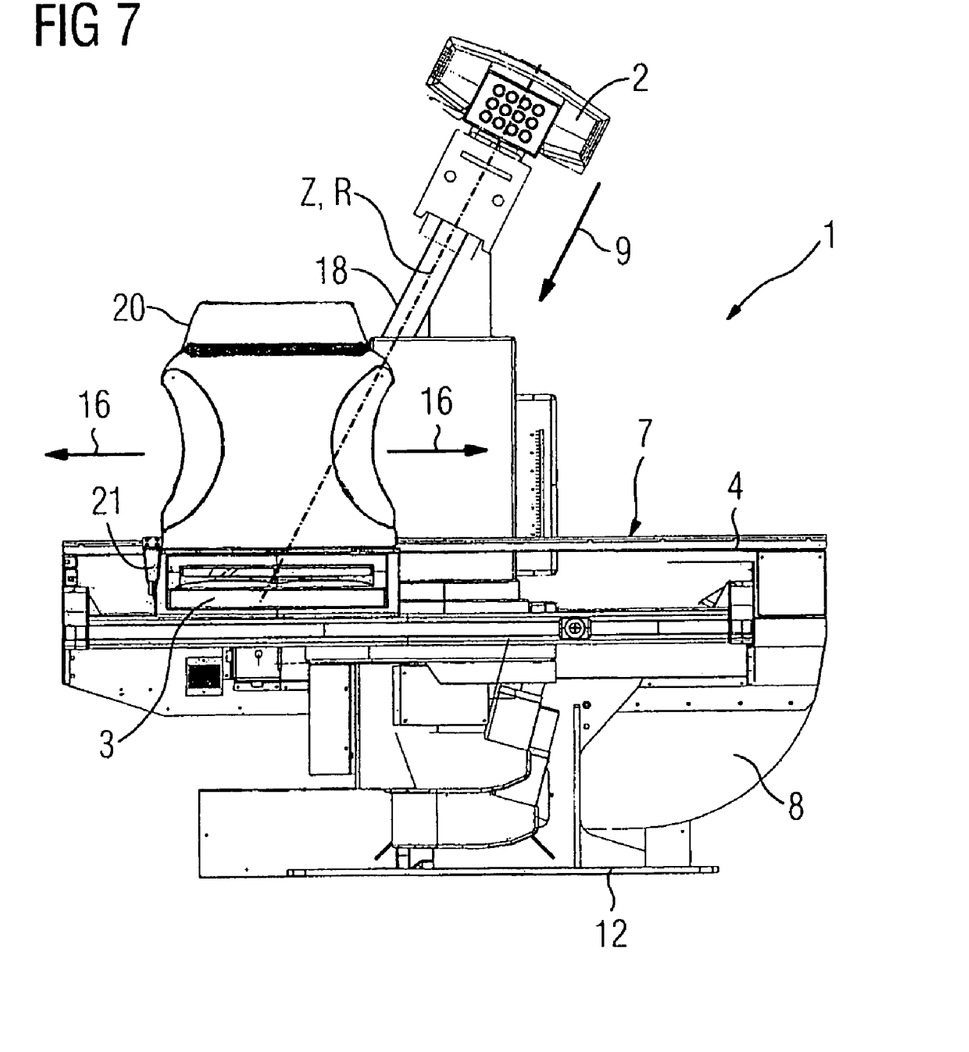
FIG. 7 shows one embodiment of an x-ray device having an image receiver and an entrained scattered ray protection device.

The patient support 4 is adjustably mounted to the dolly 14 of the stand 8 in both a longitudinal direction 16 and a transverse direction 17. The longitudinal direction 16 and the transverse direction 17 are defined here in terms of the support surface 7. The image receiver 3 and the emitter support 11 with the x-ray emitter 2 are adjustably mounted on the dolly 14 independently of one another in the longitudinal direction. When the image receiver 3 and the x-ray emitter 2 are moved longitudinally in a similar manner with respect to the patient support 4, a central beam Z of the x-ray R generated by the x-ray emitter 2 is moved in relation to the support surface 7 (FIG. 6). When the image receiver 3 and the x-ray emitter 2 are positioned longitudinally different with respect to the patient support 4, the radiation direction 9 and the central beam Z are tilted out of the vertical orientation with respect of the support surface 7 (FIG. 7). A coupling element 18 mechanically connects the image receiver 3 to the x-ray emitter 2. The coupling element 18 allows the x-ray emitter 2 to be pivoted so that the central beam Z is directed towards the image receiver 3.

In one embodiment, the x-ray device 1 includes a scattered ray protection device 20. The scattered ray protection device 20 has a flat protective screen and is at least essentially composed of transparent, x-ray-absorbent lead acrylic glass. The scattered ray protection device 20 is fixed to the image receiver 3 by a coupling unit 21. When the image receiver 3 is adjusted, the scattered ray protection device 20 is entrained in relation to the patient support 4 and/or in relation to the x-ray emitter 2. The image receiver 3 serves as a reference object, to which the scattered ray protection device 20 adopts a predetermined relative position in the longitudinal direction 16.

In this relative position, the scattered ray protection device 20 is aligned approximately flush with the front side 5 of the image receiver 3. The scattered ray protection device 20 borders a front edge 22 of the support surface 7 at a minimal distance. The scattered ray protection device 20 is aligned approximately vertically to the rotational axis 15 and approximately vertically to the support surface 7. The scattered ray protection device 20 extends, starting from the image receiver 3, in the direction of the x-ray emitter 2. The scattered ray protection device 20 shields the spatial area formed between the image receiver 3 and the x-ray emitter 2 on the front side of the x-ray device 1.

Figure 3:
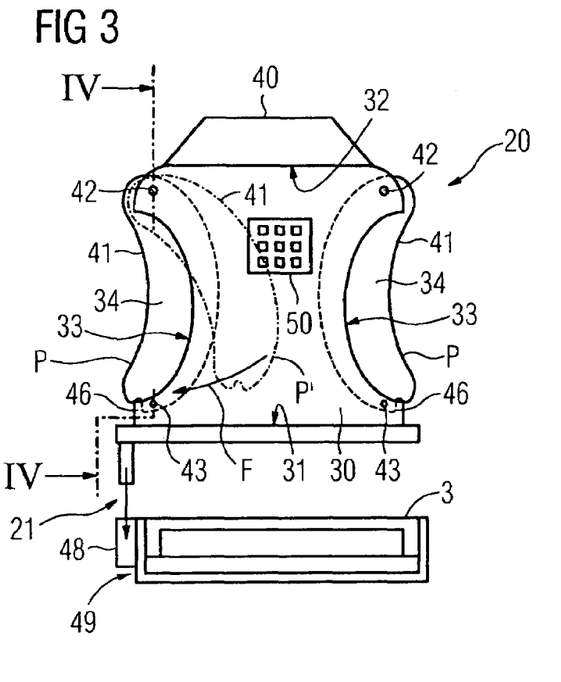
FIG. 3 is a front view of a scattered ray protection device of the x-ray device according to FIG. 1.
Figure 4:
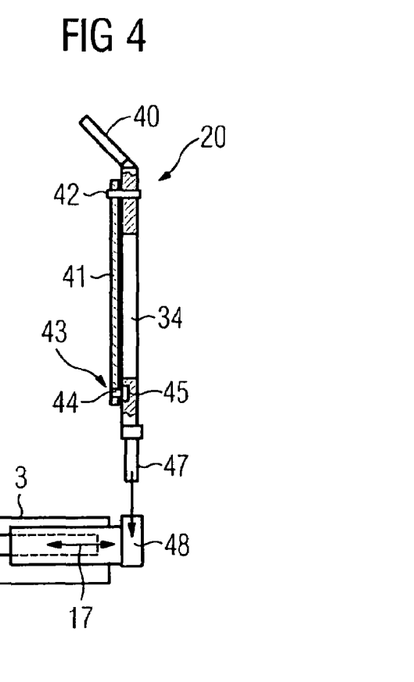
FIG. 4 is a side view of the scattered ray protection device according to FIG. 3 according to an intersecting line IV-IV (FIG. 3).

As shown in FIG. 3 and FIG. 4, the scattered ray protection device 20 includes a flat central body panel 30, which has a waisted shape. An edge of the body panel 30, which in the installation position faces the image receiver 3, is referred to here as a lower edge 31. The edge of the body panel 30 that faces away from the image receiver 3 in an installation position is referred to as an upper edge 32. The edges that connect the lower edge 31 with the upper edge 32 on both sides of the body panel 30 are referred to as side edges 33. Each side edge 33 includes a concave recess 34, which forms the waisted shape of the body panel 30.

A flat viewing panel 40 adjoins the upper edge 32 of the body panel 30. The viewing panel 40 is essentially trapezoidal. The viewing panel 40 includes transparent, x-ray-absorbent material, in particular from lead acrylic glass. The viewing panel 40 is angled with respect to the body panel 30 such that it protrudes in the direction towards the patient support 4. The viewing panel 40 allows a treating medic to bend to a certain degree across the body panel 30 in the direction towards the patient support 4 during the treatment, without being exposed to an increased scattered radiation load particularly in the head region. The treating medic has a comparatively good field of view towards the support surface 7 and a patient lying thereupon.

In one embodiment, a sliding panel 41 is affixed to each side edge 33 of the body panel 30 in a moveable fashion. Each sliding panel 41 is in turn manufactured from radiation-absorbent material. In one embodiment, the radiation-absorbent material is transparent material, in particular from lead acrylic glass. Each sliding panel 41 has an approximately banana-like shape. Each sliding panel 41 is arranged in a normal position P with respect to the body panel 30 such that it essentially covers the surface blocked out by the recess 34 of the assigned side edge 33 and increases the surface shielded from the body panel 30 at the side edges 33.

In one embodiment, as shown in FIG. 3, each sliding panel 41 is mounted on the body panel 30 to allow it to pivot around an axis 42. The axis 42 is arranged above the recess 34, for example, in a region of the body panel 30 bordering the upper edge 32. Each sliding panel 41 can be pivoted about the axis 42. In a release position P', the moved sliding panel 41 is retracted into the surface area shielded by the body panel 30. The surface blocked out by the corresponding recess 34 is essentially released.

Recesses 34 enable the treating medic to reach around the scattered ray protection device 20 during the treatment of a patient supported on the support surface 7 in a simple and unimpeded manner. The recesses 34 are covered by the moveable sliding panels 41 in a flexible manner and achieve a particularly good radiation protection for the treating medic.

The pivot mounting of each sliding panel 41 in its upper region, at least provided the patient support 4 is aligned horizontally, causes a turning moment produced by the force of gravity on the sliding panel 41 moved out of the normal position P. This turning moment is a restoring force F. The restoring force F forces the moved sliding panel 41 back into the normal position P when released. A fixing element 43 is assigned to each sliding panel 41. The fixing element 43 prevents one of the sliding panels 41 from dropping as a result of the now laterally effective gravitation in the release position P' in the case of a vertical positioning of the patient support 4 according to FIG. 2. The fixing element 43 fixes the respective sliding panel 41 into the normal position P. The sliding panel 41 may optionally be fixed automatically.

In one embodiment, the fixing element 43 is designed as a magnetic catch having two corresponding magnets 44 and 45. The magnet 44 is hereby arranged in each instance on the sliding panel 41 and the magnet 45 is assigned in each instance to a corresponding point of the body panel 30, which is selected such that in the normal position P of the sliding panel 41 the magnets 44 and 45 rest alongside each other with parallel polarity. As a result of the magnetic force of attraction of the magnets 44 and 45, the sliding panel 41 is maintained in the normal position P. Alternatively, one of magnets 44 and 45 can also be replaced by a ferromagnetic element. Instead of a magnetic catch, a spring catch, a fixing screw or any suitable catch can be used as a fixing element 43. A stop 46 of the body panel 30 assigned to each sliding panel 41 prevents the sliding panel 41 from being able to be pivoted out of the body panel 30 beyond its normal position P.

In one embodiment, as shown in FIG. 3, the coupling unit 21 serves to fix the scattered ray protection device 20 with respect to the image receiver 3. The coupling unit 21 is a plug-in connector. The coupling unit 21 allows the scattered ray protection device 20 to be detached from the image receiver 3, if necessary, in particular outside the actual radiation process in a simple and rapid manner. The coupling unit 21 includes a plug 47. The plug 47 projects beyond the lower edge 31 of the body panel 30 approximately along the length of one side edge 33. The coupling unit 21 includes a socket 48 corresponding to the plug 47. The socket 48 is affixed to a side surface 49 of the image receiver 3 and into which the plug 47 can be inserted. To prevent a rotation of the scattered ray protection device 20 in an inserted state about the axis of the plug 47, the plug 47 and the corresponding cut-out of the socket 48 preferably have an angled cross-section.

The socket 48 is affixed in an adjustable manner to the image receiver 3 by a linear guide in the transverse direction 17, so that the scattered ray protection device 20 can be adjusted in relation to the image receiver 3 for a transverse adjustment of the patient support 4. The transverse adjustability of the scattered ray protection device 20 with respect to the image receiver 3 serves to be able to guide the scattered ray protection device 20 flexibly around projecting edges of the stand 8 or the patient support 4, for example, handles. Suitable rounding or chamfering of the side edges 33 of the scattered ray protection device 20 advantageously cause the scattered ray protection device 20 to deviate automatically when it hits a projecting edge during a longitudinal movement with respect to the patient support 4. A corresponding effect can also be achieved for instance by one or a number of guidance elements assigned to the scattered ray protection device 20.

Alternatively to the one-sided attachment of the scattered ray protection device 20 to the image receiver 3 as illustrated in FIG. 3, a corresponding pin-socket-pair can also be provided in each instance on both sides of the scattered ray protection device 20 and/or image receiver 3.

In one embodiment, the scattered ray protection device 20 is a device to accommodate a number of operating and control elements 50, for example, command keys. The signal lines assigned to these operating and control elements 50 are contacted via the plug 47 and the corresponding socket 48. The plug 47 and the socket 48 are an electrical plug-socket-pair.

In one embodiment, the plug 47 and the corresponding socket 48 can be assigned an electrical safety contact. The electrical safety contact only allows the x-rays R to be switched on when the scattered ray protection device 20 is affixed to the image receiver 3.

Figure 5:
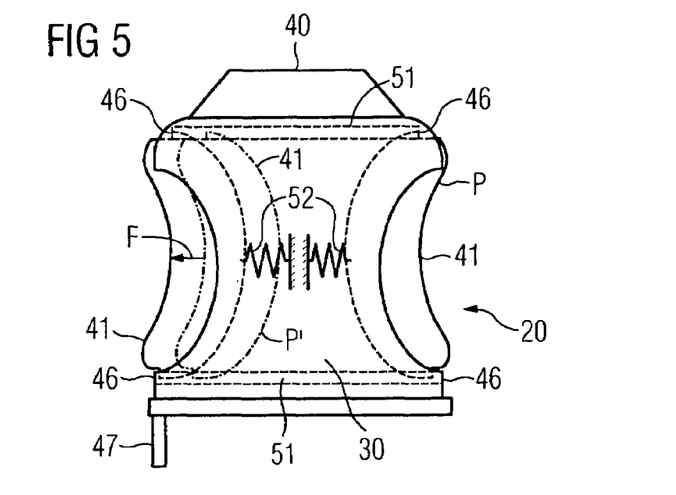
FIG. 5 shows one embodiment of the scattered ray protection device.

In one embodiment, as shown in FIG. 5, the scattered ray protection device 20 includes sliding panels 41 mounted in a non-pivoting fashion on the body panel 30. The sliding panels 41 can be moved in a lateral direction on the body panel 30 by guide rails 51. Each sliding panel 41 may include a spring element 52. The spring element 52 pretensions the respective sliding panel 41 in the normal position P and/or a restoring force F directed sideways counteracts a movement of the sliding panel 41. The restoring force restores the sliding panel 41 from the release position P' automatically into the normal position P. This restoring force F causes the respective sliding panel 41, provided it is not moved manually by overcoming the restoring force F, to always be located in the normal position P regardless of the orientation of the scattered ray protection device 20 in the surrounding room. Each sliding panel 41 is secured by stops 46 of the guide rails 51 from moving beyond the normal position P of each sliding panel 41 in the direction in which the restoring force F is acting.

In one embodiment, as shown in FIGS. 6 and 7, the x-ray device 1 has an attached scattered ray protection device 20. FIGS. 6 and 7 illustrate the effect of fixing the scattered ray protection device 20 by the coupling element 21 with respect to the image receiver. The scattered radiation protection 20 is always and automatically entrained with the image receiver 3 and is positioned in the central field of the scattered x-rays.

In one embodiment, as shown in FIG. 6, the image receiver 3 and the scattered ray protection device 20 are positioned at the foot of the patient support 4. The x-ray emitter 2 is herewith moved along with the image receiver 3 such that, compared with FIG. 1, the radiation direction 9 is oriented in an unchanged manner vertically with respect to the support surface 7. The central beam Z of the primary x-ray RI is moved correspondingly to the foot of the bed.

FIG. 7 shows the image receiver 3 and the scattered ray protection device 20 in relation to the patient support 4 in an adjustable position at the head of the bed, with the x-ray emitter 2 being left in a similar manner to FIG. 1 in a central position in relation to the patient support 4. The coupling element 18 allows the x-ray emitter 2 and thus the radiation direction 9 to be tilted such that the central beam Z is aligned approximately centrally to the image receiver 3.

The scattered ray protection device 20 is subsequently illustrated with the aid of a test measurement of the scattered radiation characteristic of the x-ray device 1 with and without the scattered ray protection device 20. The expedient dimensioning of the scattered ray protection device 20 can be determined in particular on the basis of such a test measurement.

Figure 8:
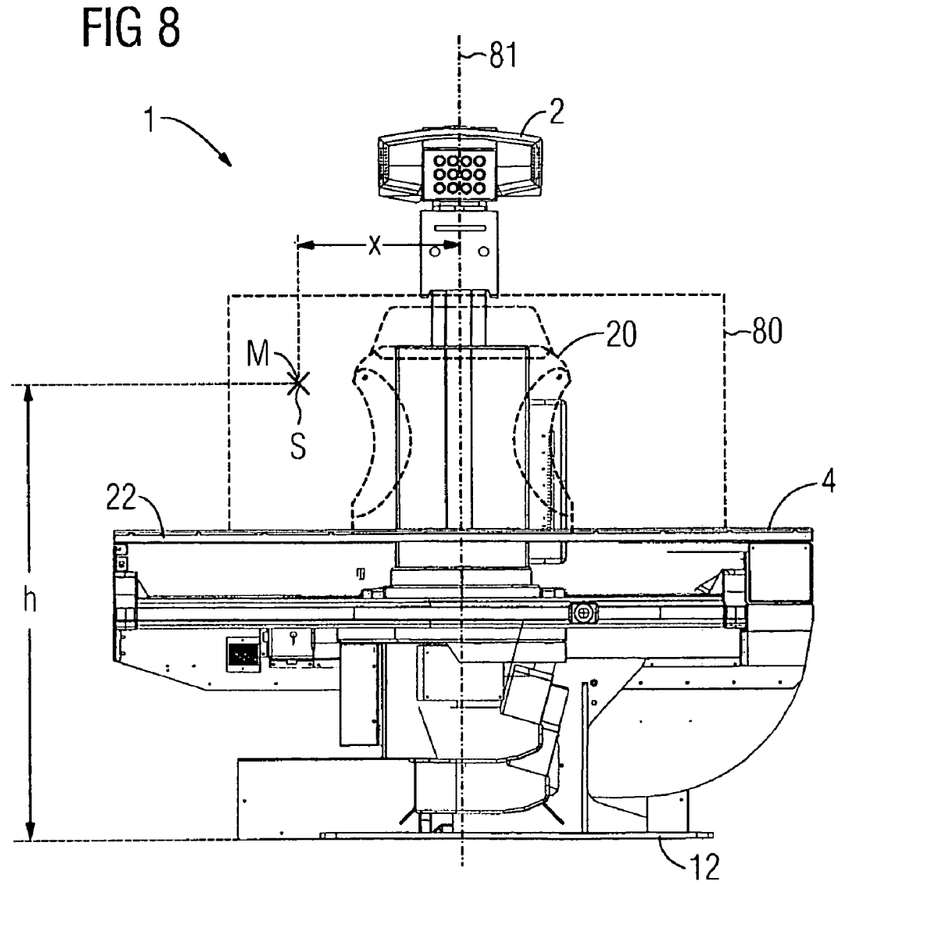
FIG. 8 is one embodiment of an x-ray device having a measuring area.

As shown in FIG. 8, a rectangular measuring area 80 is indicated with a dashed line, the horizontal extension of which amounts to 104 cm and the vertical extension of which amounts to 70 cm. In the vertical direction, the measuring area 80 covers a height range of 110 cm to 180 cm above the base plate 12, which corresponds to the working height range, in which the upper body and body region of a treating medic exposed in particular to the scattered radiation is located in practice.

FIG. 8 likewise shows as a dashed outline the area occupied by the scattered ray protection device 20 in a central position.

The measuring area 80 is arranged in parallel to the front edge 22 of the patient support 4, and is positioned at a distance of approximately 30 cm in front of the edge. The measuring area 80 is thus located at a distance from the front edge 22 of the patient support 4, as is typically also adopted by the body of a medic during the treatment.

The measuring area 80 is arranged such that the inserted scattered ray protection device 20 interconnects the x-ray emitter 2, the patient support 4 and the image emitter 3 and the measuring area 80. The test measurement was carried out on an x-ray device of the type "Iconos R 100" (SIEMENS), with a fluoroscopy time of one minute, a field parameter of 20.7× 20.7, a tube voltage of 105 kV and a tube current 1, 1 MA. Instead of a radiated patient, a pelvic phantom together with a 10 cm strong water phantom as an artificial scattered body is placed on the support surface 7 in the radiation field.

The scattered radiation dose D was measured at a number of grid-like measuring points M arranged within the measuring area 80. The scattered radiation dose D measured in this manner was measured for comparison purposes on each measuring point M in absence of the scattered ray protection device 20 and with an intervening scattered ray protection device 20.

Figure 9:
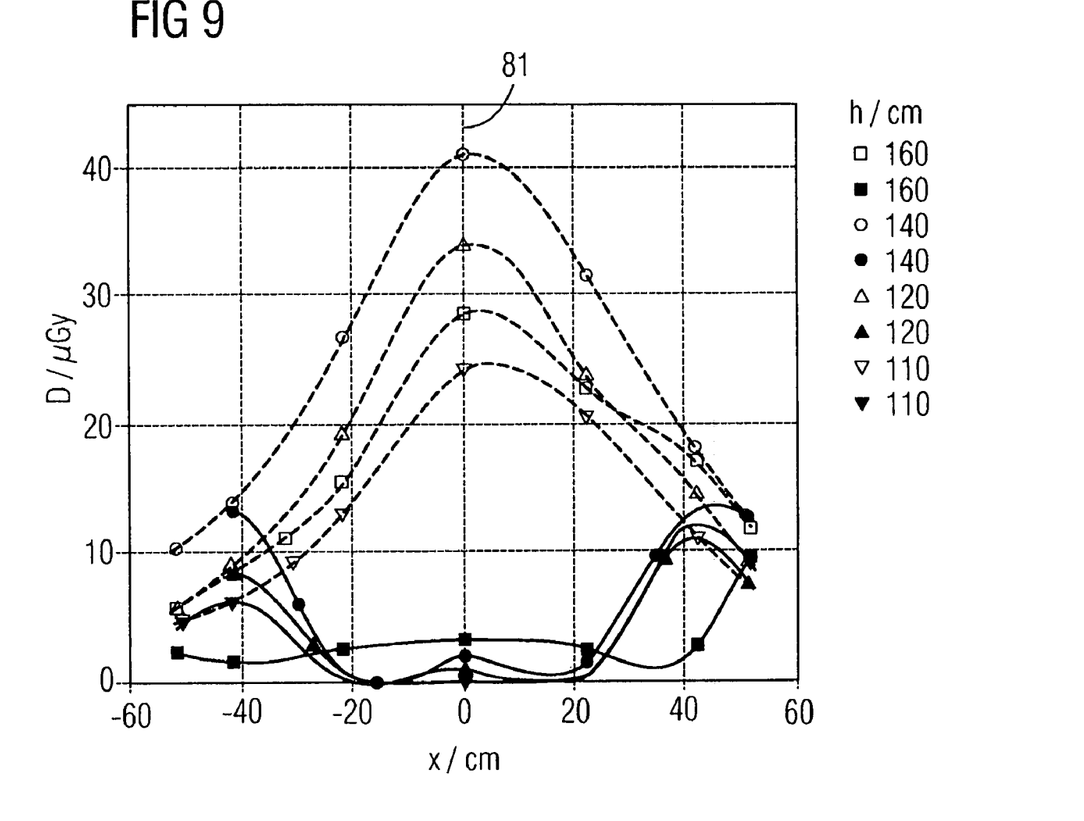
FIG. 9 shows a diagram of the scattered radiation dose at different points of the measuring area according to FIG. 8 measured with and without the scattered ray protection device on the device according to FIG. 8.

FIG. 9 illustrates the result of this test measurement in a diagram of the scattered radiation dose D as a function of the horizontal deviation x from the horizontal center line 81 of the measuring area 80. The symbols of the diagram linked by a common line represent the course of the scattered radiation dose D(x) along a horizontal line of measuring points M. Measurement values represented in this graph by the empty symbols (i.e. having a border) connected by dashed lines are measurement values that have been measured in the absence of the scattered ray protection device 20. Measurement values represented by solid symbols connected by a solid line are those which have been measured with the scattered ray protection device 20 present. The same symbol form (squared, circular) corresponds in each instance to a common working height h. The curves plotted in FIG. 9 serve to better identify associated measuring points.

It can be seen from FIG. 9 that, in the absence of the scattered ray protection device 20, the scattered radiation dose D is particularly large in the region of the center line and reduces in a bell-shaped manner on both sides with a horizontal deviation x. This allows a particularly high radiation dose D to be measured across the base plate with an average working height h≈140, while the scattered radiation dose D is lower in the case of both a lower and also a higher working height.

FIG. 9 also shows that when the scattered ray protection device 20 is used, the scattered radiation dose D in a central region of approximately x≈+/−25 cm around the center line 18 is reduced to a value clearly below 10 μGy for all working heights. The treating medic is effectively shielded against scattered radiation in this central region by means of the scattered ray protection device 20.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

The invention claimed is:

1. An x-ray device comprising:
an x-ray emitter,
an image receiver arranged in a radiation direction at a distance from the x-ray emitter,
a patient support disposed between the x-ray emitter and the image receiver, where the image receiver is adjustable with respect to the patient support in at least one spatial direction without adjusting the x-ray emitter, and
a scattered ray protection device that is fixed to the image receiver using a plug-in connector, the scattered ray protection device being a self-supporting screen that is fixed to the image receiver such that when the image receiver is adjusted with respect to the patient support, the scatter ray protection device is adjusted with respect to the patient support,
wherein the scattered ray protection device comprises a substantially flat body panel with a plane that is aligned approximately parallel to a front edge of the patient support and approximately vertical to a patient support surface of the patient support, an upper edge of the body panel facing away from the patient support comprises a viewing panel angled away from the upper edge in a direction towards the patient support,
wherein a moveable sliding panel is disposed on at least one edge of the body panel, the sliding panel enlarging a surface region of the body panel in a normal position and being moveable from the normal position into a release position, the release position being retracted at least partially into the surface region of the body panel, the sliding panel being movable from the normal position against a restoring force,
wherein the sliding panel is suspended in a pivotable manner such that a force of gravity that impacts the sliding panel is a restoring force, and
wherein the sliding panel is pretensioned by a spring element that generates the restoring force in the normal position.

2. The x-ray device as claimed in claim 1, wherein at least one side edge of the body panel comprises a recess.

3. The x-ray device as claimed in claim 1, wherein a fixing element is operable to fix the sliding panel in the normal position.

4. The x-ray device as claimed in claim 1, wherein the scattered ray protection device can be removed from the normal position predetermined by the plug-in connector with respect to the patient support.

5. The x-ray device as claimed in claim 1, wherein the scattered ray protection device comprises a transparent, x-ray beam-absorbent material.

6. The x-ray device as claimed in claim 5, wherein the x-ray beam-absorbent material is lead acrylic glass.

7. The x-ray device as claimed in claim 1, wherein the scattered ray protection device includes a number of operating and control elements.

8. An x-ray device comprising:
an x-ray emitter,
an image receiver arranged in a radiation direction at a distance from the x-ray emitter,
a patient support disposed between the x-ray emitter and the image receiver, where the image receiver is adjustable with respect to the patient support in at least one spatial direction without adjusting the x-ray emitter, and
a scattered ray protection device that is fixed to the image receiver using a plug-in connector, the scattered ray protection device being a self-supporting screen that is fixed to the image receiver such that when the image receiver is adjusted with respect to the patient support, the scatter ray protection device is adjusted with respect to the patient support,
wherein the scattered ray protection device comprises a substantially flat body panel with a plane that is aligned approximately parallel to a front edge of the patient support and approximately vertical to a patient support surface of the patient support, a moveable sliding panel being disposed on at least one edge of the body panel, the sliding panel enlarging a surface region of the body panel in a normal position and being moveable from the normal position into a release position, the release position being retracted at least partially into the surface region of the body panel, the sliding panel being movable from the normal position against a restoring force and being pretensioned by a spring element that generates the restoring force in the normal position.

9. The x-ray device as claimed in claim 8, wherein at least one side edge of the body panel comprises a recess.

10. The x-ray device as claimed in claim 8, wherein a fixing element is operable to fix the sliding panel in the normal position.

11. The x-ray device as claimed in claim 8, wherein the scattered ray protection device can be removed from the normal position predetermined by the plug-in connector with respect to the patient support.

12. The x-ray device as claimed in claim 8, wherein the scattered ray protection device comprises a transparent, x-ray beam-absorbent material.

13. The x-ray device as claimed in claim 12, wherein the x-ray beam-absorbent material is lead acrylic glass.

14. The x-ray device as claimed in claim 8, wherein the scattered ray protection device includes a number of operating and control elements.

* * * * *